United States Patent [19]
Sarin et al.

[11] Patent Number: 5,451,527
[45] Date of Patent: Sep. 19, 1995

[54] HCG PEPTIDES FOR USE IN ANTIBODY PURIFICATION PROCEDURES

[75] Inventors: Virender K. Sarin, Libertyville; John B. Bodner, Vernon Hills, both of Ill.

[73] Assignee: Abbott Laboratories, Abbott, Ill.

[21] Appl. No.: 647,893

[22] Filed: Jan. 30, 1991

Related U.S. Application Data

[60] Division of Ser. No. 375,731, Jul. 10, 1989, abandoned, which is a continuation-in-part of Ser. No. 221,687, Jul. 20, 1988, abandoned.

[51] Int. Cl.⁶ .................. G01N 33/543; G01N 33/53; A61K 37/02; C07K 3/00
[52] U.S. Cl. .................... 436/518; 436/547; 436/807; 436/824; 530/324; 530/391.1; 530/399; 530/403; 530/413
[58] Field of Search ............... 436/510, 518, 547, 807, 436/824; 530/324, 399, 403, 413, 391.1

[56] References Cited

PUBLICATIONS

Bidart et al. *Mol. Immunol.* 24(4). 1987 339–346 (abstract only).
Oztark et al. *Endocrinology* 120 (2) 1987 559–566 (abstract only).
Story et al. *J. Clin. Endrcrinol. Metab.* 53 (5) 1981 1090–1095 (abstract only).
Emlen et al. *J. Immunol Methods* 62 (2) 1983 205–216 (abstract only).
Computer generated sequence comparison of β–hcG.
Gaysen et al. *P.N.A.S. U.S.A.* vol. 81, pp. 3998–4002, Jul. 1984.
Fiddes et al., *Nature,* vol. 286, 14 Aug. 1980, pp. 684–687.
Birken et al. *"The Journal of Biological Chemistry",* vol. 256, No. 4, 25 Feb. 1981, pp. 1816–1823.

*Primary Examiner*—W. Gary Jones
*Assistant Examiner*—Bradley L. Sisson

[57] ABSTRACT

An affinity column antibody purification method using a synthetic hCG analyte-analog insolubilized on a support material. The immobilized hCG analyte-analogs are peptide sequences which duplicate or mimic the determinants formed by the amino acid residues of the C-terminus peptide sequence or portions or variants thereof. The antibodies produced according to the present invention are useful in immunoassays for hCG.

18 Claims, No Drawings

HCG PEPTIDES FOR USE IN ANTIBODY PURIFICATION PROCEDURES

REFERENCE TO RELATED APPLICATION

This application is a divisional of application Ser. No. 07/375,731, filed 10 Jul. 1989, now abandoned, which is a continuation-in-part of application Ser. No. 07/221,687, filed 20 Jul. 1988, now abandoned.

BACKGROUND OF THE INVENTION

1. Field of the Invention

This invention relates to antibody purification techniques. In particular, the invention relates to synthetic human chorionic gonadotropin (hCG) peptides for the purification of polyclonal anti-hCG antibodies.

2. Description of Related Art

Various analytical procedures and devices are commonly employed in assays to determine the presence and/or concentration of substances of interest or clinical significance which may be present in biological fluids or other materials. Such substances are commonly termed "analytes" and can include antibodies, antigens, drugs, hormones, etc. The detection of particular analytes in biological fluids such as serum, plasma, urine, spinal fluid and the like has in recent years become of critical importance in both research and clinical settings. The detection of analytes of interest can often be related to various disease states and consequently is extremely useful in the diagnosis of disease and in monitoring the effectiveness of therapy. When the analytes are antigens or antibodies, assays typically depend upon the immunological reactivity which characterizes these substances. Generally, such assays are collectively termed immunoassays.

Immunoassay techniques take advantage of the mechanisms of the immune systems of higher organisms, wherein antibodies are produced in response to the presence of antigens which are pathogenic or foreign to the organisms. One or more antibodies are produced in response to and are capable of reacting with a particular antigen, thereby creating a highly specific reaction mechanism which can be used in vitro to determine the presence or concentration of that antigen in a biological sample.

The results of an immunoassay, however, can vary according to the type of antibody used and the antibody's specificity for the particular antigen. In a quantitative assay for hCG, the particular anti-hCG antibody used may cross-react with a second glycoprotein antigen, such as human leutenizing hormone (hLH), follicle stimulating hormone (FSH) or thyroid stimulating hormone (TSH), thereby decreasing the accuracy of the assay. For example, an antibody that recognizes and binds with hCG generally will also bind to LH, FSH and TSH rather than specifically binding with hCG. Antibody purification methods have been devised to minimize cross-reactivity. Typical of such conventional methodologies is one which uses a two column technique involving a first affinity column containing a whole molecule hCG to concentrate a specific group of IgG molecules, and a second affinity column containing LH or FSH in an attempt to remove antibodies that cross-react with hCG. The hCG polyclonal antibodies obtained from this conventional procedure still have significant cross-reactivity. In addition, the two column technique is a time consuming and expensive procedure.

Chemical analysis of analytes, such as hCG and hLH, has shown that the cross-reactivity of these hormones is due to their α-subunits which are structurally similar. Therefore, attempts have been made to separate and purify the β-subunit of hCG (β-hCG) which is comparatively distinct in structure from hLH. The separation procedures, however, can still result in the occurrence of impurities and the inclusion of amino acid sequences common to both hCG and hLH.

The peptide moiety situated at the COOH terminus of β-hCG consists of about 45 amino acids. It was found that this moiety permits a distinct identification of hCG versus hLH (Matsuura et al, Endocrinology 104: 396, 1979). Iwasa et al, describe the production of a synthetic peptide sequence which reproduces a specific portion of the COOH terminal peptide (CTP) of β-hCG for use in the preparation of an anti-hCG antibody (U.S. Pat. No. 4,517,290). The amino acid sequence of the CTP of β-hCG consists of 45 amino acids, as follows:

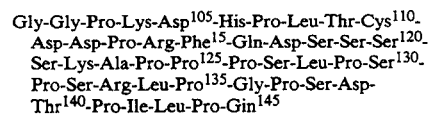

as described by Morgan et al, Mol. Cell. Biochem. 2(1), 97–99 (1973). The synthetic peptide sequence described by Iwasa for polyclonal antibody purification comprises CTP fragments or subsequences of from 10 to 23 amino acid residues, such as:

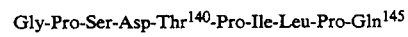

with increased sequence lengths up to Ala-Pro-Pro$^{125}$-Pro-Ser-Leu-Pro-Ser$^{130}$-Pro-Ser-Arg-Leu-Pro$^{135}$-Gly-Pro-Ser-Asp-Thr$^{140}$-Pro-Ile-Leu-Pro-Gln$^{145}$.

None of the art described above discloses or suggests the use of CTP sequences greater than 23 amino acid residues in size to alleviate the cross-reactivity characteristics of antibodies.

SUMMARY OF THE INVENTION

It has now been discovered, and the present invention is based upon this discovery, that particular synthetic amino acid sequences can be advantageously used to produce highly specific anti-hCG antibodies. Accordingly, the present invention is directed to a method for purifying an anti-hCG antibody using hCG analyte-analogs and to the production of the hCG analyte-analogs. The purification method involves an affinity column containing an hCG analyte-analog insolubilized on a carrier or support, wherein the hCG analyte-analog has the following peptide sequence:

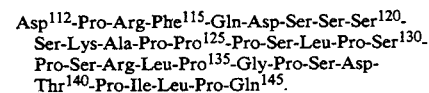

Those anti-hCG antibodies having an epitope in common with the peptide sequence are specifically absorbed from a fluid containing anti-hCG antibodies.

Other suitable hCG analyte-analog peptide sequences of the present invention include variants of the C-terminus peptide such as:

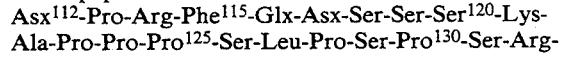

Leu-Pro-Gly$^{135}$-Pro-Pro-Asx-Thr-Pro$^{140}$-Ile-Leu-Pro-Glx-Ser$^{145}$-Leu-Pro.

wherein Asx can be Asp or Asn and Glx can be Gln or Glu. Further suitable peptide sequences of the present invention can also include one or more terminal Lys residues to facilitate the immobilization of the peptide the support for use in the affinity column. For example, the hCG analyte-analog peptide sequence can comprise:

Asx$^{112}$-Pro-Arg-Phe$^{115}$-Glx-Asx-Ser-Ser-Ser$^{120}$-
Lys-Ala-Pro-Pro-Pro$^{125}$-Ser-Leu-Pro-Ser-Pro$^{130}$-
Ser-Arg-Leu-Pro-Gly$^{135}$-Pro-Pro-Asx-Thr-
Pro$^{140}$-Ile-Leu-Pro-Glx-Ser$^{145}$-Leu-Pro wherein Asx is Asp-and Glx is Gln, and wherein the peptide sequence also includes at least one terminal Lys residue. Furthermore, peptide sequences and variant sequences of less than 23 amino acid residues can be used.

The anti-hCG antibodies produced in accordance with the present invention can be used advantageously in assays, as more fully described herein.

DETAILED DESCRIPTION OF THE INVENTION

The present invention provides a method for purifying anti-hCG antibodies using hCG analyte-analogs. The claimed method enables the production of a purified polyclonal anti-hCG antibody having a specificity comparable to that of a monoclonal anti-hCG antibody. The method of the invention is highly advantageous in terms of time savings and lower production costs by comparison to the conventional method described above.

The following terms used herein have the following meanings:

The term "determinants" refers to those regions of the analyte or other specific binding member which are intimately involved in specific binding reactions which are typified by the immunoreactive binding of antigens and antibodies. In essence, it is the determinants which differentiate antigens, and therefore, antibodies from one another on the basis of immunological specificity.

The term "analyte-analog" refers to a molecule which has substantially the same spatial and polar organization as one or more determinants of the analyte of interest. This duplication of the determinant(s) enables the analyte-analog to mimic the specific binding characteristics of the analyte. Therefore, the analyte-analog can bind to an analyte-specific binding member. In addition, the analyte-analog can be modified such that while it is not identical to the analyte it includes the necessary determinant(s) for binding to the analyte-specific binding member.

The term "specific binding member" refers to a member of a specific binding pair, i.e., two different molecules wherein one of the molecules through chemical or physical means specifically binds to the second molecule. Immunoreactive specific binding members include antigens, haptens, antibodies, and complexes thereof including those formed by recombinant DNA methods or peptide synthesis. An antibody can be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art.

The term "label" refers to any substance which is attached to a specific binding member and which is capable of producing a signal that is detectable by visual or instrumental means. Various suitable labels for use in the present invention can include chromogens; catalysts; fluorescent compounds; chemiluminescent compounds; radioactive labels; direct visual labels including colloidal metallic and non-metallic particles, dye particles, enzymes or substrates, or organic polymer latex particles; liposomes or other vesicles containing signal producing substances; and the like.

A large number of enzymes suitable for use as labels are disclosed in U.S. Pat. No. 4,275,149, columns 19–23, herein incorporated by reference. Also, an example of an enzyme/substrate signal producing system useful in the present invention is the enzyme alkaline phosphatase and the substrate nitro blue tetrazolium-5-bromo-4-chloro-3-indolyl phosphate or a derivative or analog thereof.

In an alternative signal producing system, the label can be a fluorescent compound where no enzymatic manipulation of the label is required to produce a detectable signal. Fluorescent molecules such as fluorescein, phycobiliprotein, rhodamine and their derivatives and analogs are suitable for use as labels in this reaction.

A visually detectable, colored particle can be used as the label component of the indicator reagent, thereby providing for a direct colored readout of the presence or concentration of the analyte in the sample without the need for further signal producing reagents. Materials for use as the colored particles are colloidal metals, such as gold, and dye particles as disclosed in U.S. Pat. Nos. 4,313,734 and 4,373,932. The preparation and use of non-metallic colloids, such as colloidal selenium particles, are disclosed in U.S. patent application Ser. No. 072,084, filed Jul. 9, 1987, commonly assigned herewith. The use of colloidal particle labels in immunochromatography is disclosed in U.S. patent application Ser. No. 072,459, filed Jul. 13, 1987, and organic polymer latex particles for use as labels are disclosed in U.S. patent application Ser. No. 248,858, filed Sep. 23, 1988, both commonly assigned herewith.

The term "indicator reagent" refers to a label attached to a specific binding member. The indicator reagent produces a detectable signal at a level relative to the amount of an analyte in the test sample. Generally, the indicator reagent is detected or measured after it is captured on a solid phase material, but unbound indicator reagent can also be measured to determine the result of an assay.

The specific binding member of the indicator reagent is capable of binding either to the analyte as in a sandwich assay, to the capture reagent as in a competitive assay, or to an ancillary specific binding member as in an indirect assay. The label, as described above, enables the indicator reagent to produce a detectable signal that is related to the amount of analyte in the test sample. The specific binding member component of the indicator reagent enables the indirect binding of the label to the analyte, to an ancillary specific binding member or to the capture reagent. The selection of a particular label is not critical, but the label will be capable of generating a detectable signal either by itself, such as a visually detectable signal generated by colored organic polymer latex particles, or in conjunction with one or more additional signal producing components, such as an enzyme/substrate signal producing system. A variety of different indicator reagents can be formed by varying either the label or the specific binding member; it will be appreciated by one skilled in the art that the choice involves consideration of the analyte to be detected and the desired means of detection.

The term "capture reagent" refers to an unlabeled specific binding member which is usually, but not in every case, attached to a solid phase. The attachment of the components is essentially irreversible and can include covalent mechanisms. The capture reagent is used to facilitate the observation of the detectable signal by substantially separating the analyte and/or the indicator reagent from other assay reagents and the remaining test sample. The specific binding member of the capture reagent can be specific either for the analyte as in a sandwich assay, for the indicator reagent or analyte as in a competitive assay, or for an ancillary specific binding member which itself is specific for the analyte, as in an indirect assay.

The term "ancillary specific binding member" refers to any member of a specific binding pair which is used in the assay in addition to the specific binding members of the capture reagent and the indicator reagent. For example, in an indirect assay an ancillary specific binding member may bind the analyte as well as a second specific binding member to which the analyte itself cannot attach, or in an inhibition assay the ancillary specific binding member may be a reference binding member, as described below. One or more ancillary specific binding members can be used in an assay.

The term "solid phase" refers to any material which is insoluble, or can be made insoluble by a subsequent reaction. An assay device of the present invention can have many configurations, several of which are dependent upon the material chosen as the solid phase. For example, the solid phase can include any suitable porous material. By "porous" is meant that the material is one through which liquids can flow and can easily pass. In the present invention, the solid phase can include a fiberglass, cellulose, or nylon pad for use in a pour and flow-through assay device having one or more layers containing one or more of the assay reagents; a dipstick for a dip and read assay; a test strip for wicking (e.g., paper) or thin layer chromatographic (e.g., nitrocellulose) techniques; or other porous material well known to those skilled in the art. The solid phase, however, is not limited to porous materials. The solid phase can also comprise polymeric or glass beads, microparticles, tubes, sheets, plates, slides, wells, tapes, test tubes, or the like, or any other material which has an intrinsic charge or which can retain a charged substance.

The following abbreviations are used in the description of the invention:

| Abbreviation | Amino Acid Name | Abbreviation | Amino Acid Name |
| --- | --- | --- | --- |
| Ala | Alanine | Ile | Isoleucine |
| Arg | Arginine | Leu | Leucine |
| Asn | Asparagine | Lys | Lysine |
| Asp | Aspartic Acid (Aspartate) | Met | Methionine |
| Asx | Aspartic Acid or Asparagine | Phe | Phenylalanine |
| Cys | Cysteine | Pro | Proline |
| Gln | Glutamine | Ser | Serine |
| Glu | Glutamic Acid (Glutamate) | Thr | Threonine |
| Glx | Glutamine or Glutamic Acid | Trp | Trytophan |
| Gly | Glycine | Tyr | Tyrosine |
| His | Histidine | Val | Valine |
|  |  | Xaa | Unknown or other |

GENERAL METHODS AND MATERIALS

Synthetic Peptides

The present invention includes chemically synthesized CTP fragments, i.e., analyte-analogs, for the purification of anti-hCG antibodies. In a preferred embodiment, such a fragment comprises the following amino acid sequence:

$Asp^{112}$-Pro-Arg-$Phe^{115}$-Gln-Asp-Ser-Ser-$Ser^{120}$-Ser-Lys-Ala-Pro-$Pro^{125}$-Pro-Ser-Leu-Pro-$Ser^{130}$-Pro-Ser-Arg-Leu-$Pro^{135}$-Gly-Pro-Ser-Asp-$Thr^{140}$-Pro-Ile-Leu-Pro-$Gln^{145}$.

Such a sequence is described by Morgan et al., Mol. Cell. Biochem. 2(1), 97–99 (1973), the disclosure of which is incorporated by reference herein. The inclusion of the 112–122 peptide region in a synthesized fragment of the present invention has been found to provide at least one, and possibly three, additional determinants which further and advantageously distinguish this hCG analyte-analog from other glycoproteins or other CTP peptide sequences. Furthermore, in a further preferred embodiment an analyte-analog of the present invention can include one or more Lys residues at either end of the sequence. It has been found that the addition of the Lys residues facilitates the insolubilization of the peptide for the performance of column chromatography. For example, in accordance with the invention a peptide sequence, containing the CTP 112–145 analyte-analog was synthesized with five additional lysine residues and coupled to a resin support to form an affinity column for purifying anti-hCG antibodies. The addition of the polylysine unit on the COOH terminus of the CTP analyte-analog was found to aid the coupling of the analyte-analog to the support (e.g., Affigel-10) in an affinity column without adversely affecting antibody performance (72–78% coupling efficiency).

In still another embodiment, an analyte-analog provided by the instant invention comprises a variant of the CTP sequence, modified as follows:

$Asx^{112}$-Pro-Arg-$Phe^{115}$-Glx-Asx-Ser-Ser-$Ser^{120}$-Lys-Ala-Pro-Pro-$Pro^{125}$-Ser-Leu-Pro-Ser-$Pro^{130}$-Ser-Arg-Leu-Pro-$Gly^{135}$-Pro-Pro-Asx-Thr-$Pro^{140}$-Ile-Leu-Pro-Glx-$Ser^{145}$-Leu-Pro.

Such a sequence was described by Bahl et al., Biochemical and Biophysical Research Communications, 48(2), 416–422 (1972), the disclosure of which is incorporated by reference herein. This CTP variant differs from the first embodiment described above in being modified such that one Ser amino acid residue is deleted from the 120 position, a Pro replaces a Ser at the 138 position, and a -Ser-Leu-Pro grouping is added to the sequence. In a further preferred embodiment, Asx is Asp, Glx is Gln and the analyte-analog includes the addition of one or more Lys residues at either end of the sequence.

The synthesis of peptide sequence determinants by peptide generation or other chemical processes are not the only ways the present invention can be practiced. Alternative methods may be more advantageous to the individual practitioner based upon his or her expertise, the materials available, and the type of determinant to be duplicated. For example, recombinant DNA techniques can be employed to reconstruct the determinant necessary for binding.

Alternatively, the necessary analyte-analog determinants can be produced by "mincing" or "digesting" the analyte into smaller pieces or fragments. Such fragments can be made, for example, by mechanical means such as sonication, by chemical means or by enzymatic means. The resultant fragmented analyte material can be passed through an affinity chromatography column in which is immobilized an appropriate antibody to which the antigenic determinants can attach. Thereafter, the analyte-analogs can be eluted from the column with suitable solvents.

Antibody Purification

Antibodies were prepared by eliciting a response in goats to an immunogen. The immunogens were administered to the animals by a series of inoculations, in a manner well known to those skilled in the art, and it should be understood that although goats were the immune hosts used in the experiments detailed herein, any in vivo or in vitro host capable of producing antibodies to the immunogens can be used. The anti-hCG antibodies can be elicited by using whole molecule hCG as the immunogen or by using an hCG analyte-analog, such as a synthetic $\beta$-subunit or a C-terminus peptide sequence of the present invention as the immunogen.

The antibodies which were generated against the $\beta$-subunit of the hCG molecule, were then passed through an affinity column in which either a CTP peptide or a CTP variant of the present invention was immobilized. After washing the column, the antibodies specific for the CTP determinants were eluted from the column. These polyclonal antibodies produced in accordance with the invention were found to have negligible cross-reactivity with hLH and can be advantageously used in immunoassays, such as heterogeneous sandwich immunoassays for the detection of whole molecule hCG, by comparison with conventionally produced antibodies. In use, the resultant purified antibodies can be coupled to an appropriate functional moiety, for example a label or a solid phase, to produce an indicator reagent or capture reagent for use in the immunoassay. The exact conditions of use will be determined by the routineer based upon the type of individual assay and its unique requirements.

It has been found that the use of the preferred CTP variant of the invention enables the production of a very reproducible single-step affinity column chromatography procedure for the purification of highly specific polyclonal antibodies which recognize the $\beta$-subunit of the hCG analyte but which do not react with hLH, thereby enhancing the specificity of an assay when such antibodies are used therein. Additionally, the polyclonal antibodies purified using the CTP variant of the invention have been found to increase assay sensitivity by comparison with use of the CTP peptide.

Other advantages of the present invention include the ease with which a peptide affinity column can be prepared using the analyte-analog and the ease with which specific antibodies can be generated using such a column in comparison to conventional methods. Thus, an affinity column can be produced according to the present invention which eliminates the need for the dual whole-molecule hCG and hLH affinity columns of the prior art, and such a column has been found to produce an antibody pool showing virtually no cross-reactivity to hLH. Furthermore, the process is rapid, reliable, reproducible and cost effective. In addition, polyclonal antibodies purified according to the present invention have been found to posses specificities approaching those observed with conventionally used monoclonal anti-hCG antibodies. This surprising result can be attributed to the limited number of epitopes present on the CTP (Bidart et al., J. Immuno. 134: 457, 1985, which is incorporated by reference herein.)

The analyte-analogs provided by the present invention can also be used to produce immunogens for eliciting antibodies specific for the analyte-analog determinant(s). Such immunogens have been made by coupling the analyte-analog to a carrier protein such as hemocyanin or bovine serum albumin (BSA). For example, such an immunogen can include a carrier protein coupled to the $\beta$-subunit of hCG or a carrier protein coupled to the CTP sequence or a portion or variant thereof. The peptide and the carrier can be linked by a variety of linking groups including carbamate, amido, amino, thioether or ether.

The following Examples describe in detail preferred embodiments of the present invention, and are intended to be illustrative rather than limitative thereof.

EXAMPLES

Example 1

Synthesis of a herpes peptide

A herpes peptide analyte-analog was produced in accordance with the present invention, corresponding to amino acids 290–300 of herpes simplex virus type I glycoprotein D (HSIGD) encoded in the region between base pairs 1108–1140 (Watson, R. J. et. al., *Science*, 218:381–384 (1982), as follows. The peptide sequence for the analyte-analog is shown below:

Gln-Pro-Glu-Leu-Ala-Pro-Glu-Asp-Pro-Glu-Asp-Gly

The amino acid glycine was linked at the C-terminus of the peptide to act as a linker between the peptide and resin support.

Boc-Gly-OCH$_2$-Pam resin was synthesized according to the following procedure described in Mitchell, A. R. et. al., *J. Ore. Chem.*, 43:2845–3852 (1978) and Mitchell, A. R. et. al., *J. Am. Chem. Soc.*, 98:7357–7362 (1976). Aminomethyl-resin (2.36 g, 0.25 mmol/g) was placed in a reaction vessel and allowed to swell in methylene chloride (CH$_2$Cl$_2$) for 30 minutes. It was then coupled to Boc-Gly-OCH$_2$·C$_6$H$_4$CH$_2$CO$_2$H (0.89 mmol) in methylene chloride by the addition of dicyclohexylcarbodiimide (DCC, 0.89 mmol).

Protected amino acids were coupled to the resin support in a stepwise manner by preformed symmetric anhydride chemistry, except in cases of aspartic acid, and glutamine. All amino-terminal residues were protected by t-butyloxy carbonyl (t-BOC) and side chains of various amino acid residues were protected by the following groups: Asp by cyclohexyl (OChxl) and Glu by benzyl (OBzl). The following coupling protocol was used for amino acids Glu, Pro, Leu, Ala.

1) CH$_2$Cl$_2$ was added, shaken for one minute and filtered (the process was repeated six times, i.e., 6×1 minute);
2) 50% trifluoroacetic acid (TFA)/CH$_2$Cl$_2$, 1×1 minute;
3) 50% TFA/CH$_2$Cl$_2$, 1×20 minutes;
4) CH$_2$Cl$_2$, 6×1 minute;
5) 5% diethylamine (DIEA)/CH$_2$Cl$_2$, 2×2 minutes;
6) CH$_2$Cl$_2$, 3×1 minutes; and
7) protected amino acid, eight equivalents, was dissolved in methylene chloride and cooled to 0° C. To this solution, N-N-dicyclohexylcarbodiimide (DCC) was added (four equivalents in methylene chloride). After stirring for ten minutes at 0° C., the solution was filtered. A final concentration of this symmetric anhydride (~0.05M to 0.1M) was added to the reaction vessel containing the resin. The vessel was shaken for two hours at room temperature and filtered.
8) CH$_2$Cl$_2$, 3×1 minute;
9) 5% DIEA/CH$_2$Cl$_2$, 1×2 minutes; and
10) CH$_2$Cl$_2$, 3×1 minute; and then
11) either step 7 was repeated or 1-hydroxybenzotriazole (HOBT four equivalents) was dissolved in dimethylformamide (DMF) and cooled to 0° C. To this solution, DCC (four equivalents) in CH$_2$Cl$_2$ was added followed by the addition of protected amino acid (four equivalents) in DMF:CH$_2$Cl$_2$ (1:1). This reaction mixture was stirred at 0° C. for ten minutes. Then the reaction mixture was transferred to the reaction vessel containing resin and shaken for two hours at room temperature.
12) CH$_2$Cl$_2$:DMF (1:1), 3×1 minute; and
13) CH$_2$Cl$_2$, 3×1 minute.

The completeness of the reaction was monitored by a quantitative ninhydrin test as described by Sarin, V. K. et. al., *Analytical Biochemistry*, 117:147–157 (1981).

For protected amino acid Asp, steps 1 to 6 were the same as described above and followed by:

7) protected amino acid (four equivalents) in methylene chloride was added to the reaction vessel with DCC (four equivalents) in methylene chloride and shaken at room temperature for 24–72 hours; and
8) CH$_2$Cl$_2$, 6×1 minute.

The completeness of the reaction was monitored by quantitative ninhydrin analysis.

For glutamine, a DCC/HOBT coupling protocol was used as described by Konig and Geiger, *Chem. Ber.*, 103: 788–798 (1970).

The fully protected peptide-resin (1 g) was allowed to swell in methylene chloride for five minutes and the N-alpha-BOC protecting group was removed using the following protocol:

1) CH$_2$Cl$_2$, 6×1 minute;
2) 50% TFA/CH$_2$Cl$_2$, 1×1 minute;
3) 50% TFA/CH$_2$Cl$_2$, 1×20 minutes;
4) CH$_2$Cl$_2$, 6×1 minute;
5) 5% DIEA/CH$_2$Cl$_2$, 1×3 minutes;
6) CH$_2$Cl$_2$, 4×1 minute; and
7) the resin was then dried.

The peptide-resin was divided into two separate reaction vessels and treated for 60 minutes at 0° C. with anhydrous hydrofluoric acid (13.5 ml) to which p-cresol (1.5 ml) had been added. The hydrofluoric acid was distilled-off in vacuo at 0° C. The cleaved free peptide and resin were washed four times with diethyl ether (10 ml aliquots), and the peptide was extracted with three extractions each of 10% and 20% aqueous acetic acid respectively. The aqueous extractions were combined and washed three times each with 10 milliliter aliquots of diethyl ether and ethylacetate. The aqueous layer was then lyophilized to provide a white fluffy peptide. The polypeptide was purified by reversed-phase high performance liquid chromatography (HPLC) according to routine protocols such as that described by Rivier, et al., *Journal of Chromatography*, 288; 303–328 (1984) which is incorporated by reference herein. The composition of the purified peptide was confirmed by hydrolysis in 6N hydrochloric acid (HCl) in vacuo at 110° C. for 24 hours and was subsequently analyzed on an amino acid analyzer.

Example 2

Synthesis of β-hCG C-terminus peptides

An hCG analyte-analog, corresponding to CTP 112–145 of β-hCG, was produced in accordance with the present invention as follows. The peptide sequence is shown below:

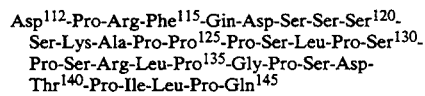

The analyte-analog was synthesized on a resin support by stepwise solid phase synthesis starting with the carboxy-terminal residue. Substantially, the procedure described in Barany and Merrifield, *The Peptides*, 2: 1984, Gross, E. and Meinehofer, J. eds, Academic Press, New York, N.Y. (1980) was used for this synthesis. A BOC-L-Gln-OCH$_2$-resin was transferred to a reaction vessel of a Beckman synthesizer, Model 900. Protected amino acids were coupled in a stepwise manner to the resin support substantially in accordance with the chemistry described in Example 1. Amine acid, Leu, at positions 128 and 134, were double coupled to ensure completeness of the coupling reaction. After incorporation of Pro at position 126, all subsequent amino acids were double coupled.

The completed peptide was cleaved off the fully protected peptide-resin with anhydrous hydrofluoric acid using the protocol described in Example 1. The crude peptide was purified using reversed-phase HPLC on a C$_4$ column (10 mm×25 cm) using a flow rate of three ml/min and employing gradients of 0.1% TFA/H$_2$O (A) and 100% acetonitrile (B) as the solvent systems. The gradient used was 10% B to 35% B over a thirty minute period.

The polypeptide elution from the HPLC column was monitored at 225 nm and 280 nm. The composition of the purified peptide was confirmed as described in Example 1.

Example 3

Synthesis of β-hCG polylysine C-terminus peptides

A polylysine analyte-analog, including five additional lysine residues attached to the C-terminus, referred to as polylysine CTP, was produced in accordance with the invention using the following procedure. The additional lysines facilitated the production of a peptide immunosorbent for use in an affinity column to purify anti-hCG antibody. The additional amino acid(s) can be added to either end of the peptide sequence, for example:

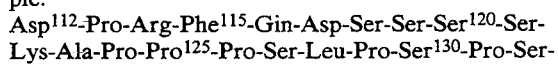

Arg-Leu-Pro$^{135}$-Gly-Pro-Ser-Asp-Thr$^{140}$-Pro-Ile-Leu-Pro-Gln$^{145}$-Lys-Lys-Lys-Lys-Lys

The peptide was assembled, cleaved and purified as described above except that it was synthesized on an Applied Biosystems synthesizer, Model 430A. A Boc-L-Lys (2 Cl-Z)-OCH$_2$-Pam-resin was transferred to a reaction vessel, and protected amino acids were coupled in a stepwise manner to the resin support by preformed symmetric anhydride chemistry (except in the case of arginine and glutamine addition where DCC/HOBT coupling protocol was used.) The fully protected peptide-resin was treated with anhydrous hydrofluoric acid followed by extraction and purification of the peptide as described above.

Example 4

Synthesis of a polylysine CTP variant

A polylysine CTP variant analyte-analog, according to the invention was synthesized having the following sequence:

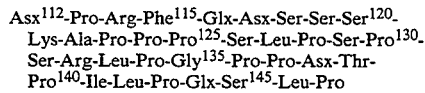
Asx$^{112}$-Pro-Arg-Phe$^{115}$-Glx-Asx-Ser-Ser-Ser$^{120}$-
Lys-Ala-Pro-Pro-Pro$^{125}$-Ser-Leu-Pro-Ser-Pro$^{130}$-
Ser-Arg-Leu-Pro-Gly$^{135}$-Pro-Pro-Asx-Thr-
Pro$^{140}$-Ile-Leu-Pro-Glx-Ser$^{145}$-Leu-Pro wherein Asx is Asp, Glx is Gln and five additional Lys residues are included on the end of the sequence. The peptide was assembled, cleaved and purified substantially in accordance with the procedure described in Example 3, except the side chain functional groups of the amino acids were protected by coupling reactions as follow: Lys and 2-Cl-Z; Ser and Bzl; Asp and OBzl; Arg and tosyl (TOS); and Thr and Bzl. Amino acids at positions 112, 123, 124, 127, 133, 135, 136, 141, 142 and 146 were recoupled using symmetric anhydride chemistry in methylene chloride substantially in accordance with the procedure described in Example 1.

The fully protected peptide-resin was treated with anhydrous hydrofluoric acid followed by extraction of the peptide, substantially in accordance with the procedure described in Example 1, except that two additional 40% aqueous acetic acid extractions were performed. The crude peptide was then purified by reversed-phase HPLC on a C$_4$ column (Vydac 22×250 mm; The Separation Group, Hesperia, Calif.), substantially in accordance with the procedure described in Example 1, using a flow rate of 12 ml/min and employing gradients of 0.1% TFA/H$_2$O (A) and 100% acetonitrile (B) as the solvent systems. The gradient was started at 19% B, where it was maintained for three minutes and then increased to 40% B over a twenty minute period using curve number seven of Water's automated gradient controller (Water's Millipore Corporation, Bedford, Mass.). The gradient was maintained at 40% B for one minute and then brought back to 19% B over a one minute period. The polypeptide elution from the HPLC column was monitored at 225 nm and 254 nm simultaneously. The composition of the purified peptide was confirmed by amino acid analysis as described in Example 1.

Example 5

CTP:hemocyanin immunogen

The CTP produced substantially in accordance with the procedure described in Example 2 was coupled to hemocyanin (from Limulus Polyphemus Hemolymph type VIII; Sigma, St. Louis, Me.) by a 1-ethyl-3-(3-dimethylaminopropyl)carbodiimide (EDC) method. One milligram of CTP was dissolved in phosphate buffered saline (1.0 ml). Hemocyanin (2.0 mg) was weighed and transferred to the CTP solution. Twenty milligrams of EDC was measured and dissolved in water (200 μl). The EDC solution was then slowly added to the CTP-hemocyanin solution while mixing. The mixture was reacted for one hour and was then dialyzed against water in a cellulose dialyzing tube (Spectra/per ®, Spectrum Medical Industries, Inc., Los Angeles, Calif.; mw 12,000–14,000). The dialysis occurred over 24 hours with three volume changes. After dialysis, the solution was clarified by centrifugation. The resulting conjugate was assayed by Biuret assay for protein content.

Example 6

Anti-hCG Antibody Purification

An affinity column for antibody purification was made using an analyte-analog of the present invention, according to the following procedure. The HPLC-purified polylysine CTP variant peptide (made substantially in accordance with the procedure described in Example 4) was dissolved in 0.1M 3-(N-morpholino)-propanesulfonic acid (MOPS) buffer, pH 7.5. The resulting solution was then combined with a slurry of Affigel-10 resin (Bio-Rad, Richmond, Calif.) that had previously been washed and activated in 0.1M MOPS, pH 7.5. The ratio of peptide (rag) to Affigel-10 (ml) was approximately 7:1. After coupling overnight at 2°–8° C., the peptide coupled resin was washed three times with 0.1M MOPS, pH 7.5, and then was equilibrated in Tris-saline buffer containing 0.1M tris-(hydroxy-methyl)aminomethane (pH 7.5), 0.5M NaCl and 0.1% NaN$_3$, and an initial absorbance at the wavelength of 280 nanometers (A$_{280}$) was determined.

Anti-serum raised in goats against the β-subunit of hCG was precipitated with ammonia sulfate at 2°–8° C. The precipitated antibody was recovered by centrifugation, and the pellet was resuspended in Tris-saline buffer. The resuspended antibody was exhaustively dialysed against the Tris-saline buffer at 2°–8° C. and was then stored at −15° C.

Column chromatography purification of the antibody was performed at room temperature. The frozen antibody was thawed and was allowed to equilibrate to room temperature. The antibody was passed over the affinity column at a flow rate of 1.5 milliliters/minute. Unbound material was removed by washing the column with the Tris-saline buffer until the initial A$_{280}$ baseline was re-established. The bound antibody was eluted in a 0.1M glycine-HCl (pH 2.5) buffer at a flow rate of 1.5 milliliters/minute. The antibody containing fractions were pooled and immediately neutralized with 0.5M Tris. The neutralized antibody solution was exhaustively dialysed against 0.02M sodium phosphate, pH 7.2, 0.15M NaCl at 2°–8° C. The dialysed antibody solution was then concentrated to approximately 10 milligrams/milliliter and was stored at −15° C.

Comparison of Purified Antibodies

Equivalent protein masses of CTP peptide purified antibody and CTP variant purified antibody, produced substantially in accordance with the procedure described in Example 6, were used to demonstrate the performance of the antibodies produced using the principles of the present invention. To accomplish the foregoing, the CTP peptide antibody and the CTP variant antibody were conjugated to alkaline phosphatase, as described below, to form two different antibody/enzyme indicator reagents for use in a heterogeneous sandwich immunoassay.

Oxidation of the alkaline phosphatase was performed in 25 mM sodium periodate, 0.2 mM sodium acetate, and 0.2M sodium phosphate, pH 4.5, for three hours at room temperature in the dark. Oxidation was terminated by by the addition of glycerol, and the resultant material was dialyzed overnight against 10 mM sodium acetate, pH 4.5, 100 mM NaCl, 1 mM $MgCl_2$ and 1 mM $ZnCl_2$. The dialyzed alkaline phosphatase was combined with the respective purified antibodies at a 1:1 ratio with a final antibody concentration between 1.5 to 2.0 milligram/milliliter. The pH of the solution was increased to pH 9.5 by the addition of sodium bicarbonate, and the solution was allowed to incubate for five hours in the dark at room temperature. The respective indicator reagents were transferred to 2°-8° C. and reduced by the addition of sodium sodium borohydride for three hours. The reduced indicator reagents were then dialyzed overnight at 2°-8° C. against 50 mM Tris-HCl, pH 7.5, 0.1 mM $MgCl_2$, 0.1 mM $ZnCl_2$ and 0.1% (w/v) $NaN_3$.

The resulting indicator reagents were titered to produce equivalent signals when used in an hCG sandwich immunoassay which was performed on an Abbott IMx ™ automated microparticle enzyme immunoassay system (Abbott Laboratories, Abbott Park, Ill.). The capture reagent was a monoclonal anti-$\beta$-hCG antibody coated upon microparticles (in 50 mM Tris-HCl, pH 7.5, 0.5 mM NaCl, 0.1% $NaN_3$ and 13.6% sucrose). The sample (50 $\mu$l) was mixed with the capture reagent (50 $\mu$l), one of the indicator reagents (50 $\mu$l; in 50 mM Tris-HCl, pH 7.4, 0.5 M NaCl, 2.25% [w/v] fish gelatin, 1% [w/v] Brij-35, 1.0 mM $MgCl_2$, 0.1 mM $ZnCl_2$ and 0.1% [w/v] $NaN_3$ and 10 $\mu$l [75/25 v/v] normal human serum/normal goat serum) and a diluent (10 $\mu$l; 0.05M Tris-HCl, at pH 7.5, containing 0.3M NaCl and 0.1% sodium azide). The reaction mixture was dispensed into a reaction well and was incubated for five minutes. An aliquot of the reaction mixture (110 $\mu$l) was transferred to a glass fiber matrix to which the microparticles bind, and the matrix was washed with diluent. A fluorescent substrate, 4-methylumbelliferyl phosphate (65 $\mu$l) was added to the matrix and the sample was read by a fluorometer. The rate of fluorescence emitted from the surface of the matrix was directly proportional to the concentration of analyte in the sample.

Calibrators containing known amounts of hCG (in a normal calf serum matrix) were measured and used to calculate a standard curve for each of the indicator reagents. The calibration results are presented in Table 1. An indicator reagent titer of 1/2000 was used for the reagent containing the CTP variant antibody as the specific binding member, and an indicator reagent titer of 1/1000 was used for the reagent containing the CTP peptide antibody as the specific binding member. As shown in Table 1, the indicator reagent made from the CTP variant antibody provided a higher signal/noise (S/N) ratio by producing a lower background at zero mIU/ml of hCG. The rate or counts/second/second (c/s/s) is a measurement of the intensity of the fluorescent emission produced by the enzyme/substrate reaction (described by Fiore et al., *Clinical Chemistry*, 34 (9); 1726-1732, 1988, which is incorporated by reference herein). The S/N is defined as the measured rate for each sample divided by the measured rate for the zero calibrator.

TABLE 1

Comparison of Indicator Reagent Performance

| Calibrators mIU/ml of hCG | CTP Peptide Antibody | | CTP Variant Peptide Antibody | |
|---|---|---|---|---|
| | Rates c/s/s | S/N | Rates c/s/s | S/N |
| 0 | 4.5 | — | 2.4 | — |
| 10 | 22.0 | 4.9 | 29.5 | 12.1 |
| 75 | 157.1 | 35.3 | 204.8 | 83.9 |
| 250 | 576.2 | 129.5 | 708.2 | 290.3 |
| 500 | 1099.6 | 247.1 | 1114.9 | 456.9 |
| 1000 | 2080.1 | 467.4 | 2016.9 | 826.6 |

A set of controls was also tested, and the results are presented in Table 2 as determined from the standard curves produced by the calibrators. The controls contained approximately 25, 150 or 750 mIU/ml of hCG. The results demonstrated that the two different indicator reagents, both made from antibodies purified according to the present invention, produced equivalent signals, but that a much lower concentration of the indicator reagent containing the CTP variant antibody (a two fold lower concentration) was needed to produce the signal.

TABLE 2

Measurement of Controls with Standard Curve

| Controls mIU/ml of hCG | CTP Peptide Antibody mIU/ml of hCG from standard curve | CTP Variant Peptide Antibody mIU/ml of hCG from standard curve |
|---|---|---|
| 25 | 22.7 | 23.0 |
| 150 | 142.9 | 143.7 |
| 750 | 756.5 | 766.2 |
| Sensitivity (by 2 standard deviations) | 0.4 | 0.2 |

The assay results also demonstrated that the indicator reagent made from a preferred antibody produced according to the present invention, that is purified using the CTP variant, provided an increase in assay sensitivity as defined as the 95% confidence limit at zero mIU/milliliter hCG In addition, hLH cross-reactivity was determined by performing the same assay using known hLH test samples and measuring the resultant hCG values. The hLH cross-reactivity was found to be 3 to 8 times lower when the CTP variant antibody was used in the indicator reagent, as demonstrated by the results presented in Table 3.

TABLE 3

| | Cross-reactivity | |
|---|---|---|
| hLH Test Samples mIU/ml | CTP Peptide Antibody mIU/ml of hCG from standard curve | CTP Variant Peptide Antibody mIU/ml of hCG from standard curve |
| 500 | 0.48 | 0.06 |
| 1000 | 0.98 | 0.30 |

It will be appreciated by one skilled in the art that many of the concepts of the present invention are equally applicable to the production of analyte-analogs and the purification of antibodies for analytes other than hCG. Accordingly, the preferred embodiments described and the alternative embodiments presented are intended as examples rather than as limitations. Thus, this description of the invention is not intended to limit the invention to the particular embodiments disclosed, but it is intended to encompass all equivalents and subject matter within the spirit and scope of the invention as described above and as set forth in the following claims.

What is claimed is:

1. A method for purifying anti-hCG antibody, comprising the steps of:

a. contacting a body fluid containing anti-hCG antibody with an hCG analyte-analog immobilized upon a support, wherein said hCG analyte-analog has a peptide sequence comprising:

Asx Pro Arg Phe Glx Asx Sea Ser Ser Lys Ala Pro Pro Pro Ser Leu Pro
   112     115         120                 125

Ser Pro Ser Arg Leu Pro Gly Pro Pro Asx Thr Pro Ile Leu Pro Glx Ser
   130             135                 140                 145
   Leu Pro whereby anti-hCG antibody specific for said hCG analyte-analog is absorbed; and b. eluting said anti-hCG antibody thus specifically absorbed.

2. The method according to claim 1, wherein said anti-hCG antibody is elicited with an immunogen selected from the group consisting of hCG and an hCG analyte-analog coupled to a carrier protein.

3. The method according to claim 2, wherein said immunogen is a β-subunit of hCG.

4. The method according to claim 2, wherein said hCG analyte-analog is the C-terminus peptide sequence 112–145 of β-hCG.

5. The method according to claim 1, wherein said hCG analyte-analog has a peptide sequence comprising:

Asp Pro Arg Phe Gln Asp Ser Ser Ser Lys Ala Pro Pro Pro Ser Leu Pro
   112     115         120                 125

Ser Pro Ser Arg Leu Pro Gly Pro Pro Asp Thr Pro Ile Leu Pro Gln Ser
   130             135                 140                 145

Leu Pro.

6. An hCG analyte-analog peptide, having the sequence:

Asp Pro Arg Phe Gln Asp Ser Ser Ser Lys Ala Pro Pro Pro Ser Leu Pro
   112     115         120                 125

Ser Pro Ser Arg Leu Pro Gly Pro Pro Asp Thr Pro Ile Leu Pro Gln Ser
   130             135                 140                 145

Leu Pro with at least one Lys residue coupled to either terminal amino acid residue.

7. The peptide according to claim 6, having the sequence:

Lys Lys Lys Lys Lys Asp Pro Arg Phe Gln Asp Ser Ser Ser Lys Ala Pro
               110         112     115                 120

Pro Pro Ser Leu Pro Ser Pro Ser Arg Leu Pro Gly Pro Pro Asp Thr Pro
       125                 130             135                 140

Ile Leu Pro Gln Ser Leu Pro.
                   145

8. The peptide according to claim 6, having the sequence:

Asp Pro Arg Phe Gln Asp Ser Ser Ser Lys Ala Pro Pro Pro Ser Leu Pro
   112     115         120                 125

Ser Pro Ser Arg Leu Pro Gly Pro Pro Asp Thr Pro Ile Leu Pro Gln Ser
   130             135                 140                 145

Leu Pro Lys Lys Lys Lys Lys.
                   150

9. An affinity column for purifying anti-hCG antibodies, comprising:

a. an hCG analyte-analog peptide having the sequence

Asp Pro Arg Phe Gln Asp Ser Ser Ser Lys Ala Pro Pro Pro Ser Leu Pro
   112     115         120                 125

Ser Pro Ser Arg Leu Pro Gly Pro Pro Asp Thr Pro Ile Leu Pro Gln Ser
   130             135                 140                 145

Leu Pro wherein said peptide is immobilized upon
   b. a support.

10. The affinity column according to claim 9, wherein said hCG analyte-analog peptide is immobilized upon said support through at least one Lys residue coupled to either terminal amino acid residue of said hCG analyte-analog.

Asx Pro Arg Phe Glx Asx Ser Ser Ser Lys Ala Pro Pro Pro Ser Leu Pro
112      115               120              125

Ser Pro Ser Arg Leu Pro Gly Pro Pro Asx Thr Pro Ile Leu Pro Glx Ser
    130              135              140                    145

Leu Pro

11. The affinity column according to claim 10, wherein said peptide sequence comprises:

Lys Lys Lys Lys Lys Asp Pro Arg Phe Gln Asp Ser Ser Ser Lys Ala Pro
        110      112      115                  120

Pro Pro Ser Leu Pro Ser Pro Ser Arg Leu Pro Gly Pro Pro Asp Thr Pro
125              130                      135              140

Ile Leu Pro Gln Ser Leu Pro.
            145

12. The affinity column according to claim 10, wherein said peptide sequence comprises:

Asp Pro Arg Phe Gln Asp Ser Ser Ser Lys Ala Pro Pro Pro Ser Leu Pro
112      115              120              125

Ser Pro Ser Arg Leu Pro Gly Pro Pro Asp Thr Pro Ile Leu Pro Gln Ser
    130              135              140                    145

Leu Pro Lys Lys Lys Lys Lys.
                150

13. A method for purifying anti-hCG antibody, comprising the steps of:

a. contacting a body fluid containing anti-hCG antibody with an hCG analyte-analog immobilized upon a support, wherein said hCG analyte-analog has a peptide sequence comprising:

Asp Pro Arg Phe Gln Asp Ser Ser Ser Lys Ala Pro Pro Pro Ser Leu
112      115              120              125

Pro Ser Pro Ser Arg Leu Pro Gly Pro Ser Asp Thr Pro Ile Leu Pro Gln
    130                  135              140                    145 has a peptide sequence comprising:

with at least one Lys residue coupled to either terminal amino acid residue or with at least one Lys residue coupled to either terminal amino acid residue, and wherein said hCG analyte-analog is immobilized upon the support through said terminal Lys residue, whereby anti-hCG antibody specific for said hCG analyte-analog is absorbed; and b. eluting said anti-hCG antibody thus specifically absorbed.

14. The method according to claim 13, wherein said hCG analyte-analog has a peptide sequence comprising:

Lys Lys Lys Lys Lys Asp Pro Arg Phe Gln Asp Ser Ser Ser Lys Ala
        110      112      115                  120

Pro Pro Pro Ser Leu Pro Ser Pro Ser Arg Leu Pro Gly Pro Ser Asp Thr
125                  130                      135              140

Pro Ile Leu Pro Gln
            145 or

Lys Lys Lys Lys Lys Asx Pro Arg Phe Glx Asx Ser Ser Ser Lys Ala Pro
        110      112      115                  120

Pro Pro Ser Leu Pro Ser Pro Ser Arg Leu Pro Gly Pro Pro Asx Thr Pro
125              130                      135              140

Ile Leu Pro Glx Ser Leu Pro.
            145

15. The method according to claim 13, wherein said hCG analyte-analog has a peptide sequence comprising:

Asp Pro Arg Phe Gln Asp Ser Ser Ser Lys Ala Pro Pro Pro Ser Leu
112      115              120              125

| Ser | Pro | Ser | Arg | Leu | Pro | Gly | Pro | Pro | Ser | Asp | Thr | Pro | Ile | Leu | Pro | Gln |
|-----|-----|-----|-----|-----|-----|-----|-----|-----|-----|-----|-----|-----|-----|-----|-----|-----|
|     | 130 |     |     |     | 135 |     |     |     |     | 140 |     |     |     |     |     | 145 |

| Lys | Lys | Lys | Lys | Lys |
|-----|-----|-----|-----|-----|
|     |     |     |     | 150 | or

| Asx | Pro | Arg | Phe | Glx | Asx | Ser | Ser | Ser | Lys | Ala | Pro | Pro | Pro | Ser | Leu | Pro |
|-----|-----|-----|-----|-----|-----|-----|-----|-----|-----|-----|-----|-----|-----|-----|-----|-----|
| 112 |     |     | 115 |     |     |     |     | 120 |     |     |     |     | 125 |     |     |     |

| Ser | Pro | Ser | Arg | Leu | Pro | Gly | Pro | Pro | Asx | Thr | Pro | Ile | Leu | Pro | Glx | Ser |
|-----|-----|-----|-----|-----|-----|-----|-----|-----|-----|-----|-----|-----|-----|-----|-----|-----|
|     | 130 |     |     |     | 135 |     |     |     |     | 140 |     |     |     |     |     | 145 |

| Leu | Pro | Lys | Lys | Lys | Lys | Lys. |
|-----|-----|-----|-----|-----|-----|------|
|     |     |     |     | 150 |     |      |

16. The method according to claim 13, wherein said hCG analyte-analog has a peptide sequence comprising:

| Lys | Lys | Lys | Lys | Lys | Asp | Pro | Arg | Phe | Gln | Asp | Ser | Ser | Ser | Lys | Ala | Pro |
|-----|-----|-----|-----|-----|-----|-----|-----|-----|-----|-----|-----|-----|-----|-----|-----|-----|
|     |     |     | 110 |     | 112 |     |     | 115 |     |     |     |     | 120 |     |     |     |

| Pro | Pro | Ser | Leu | Pro | Ser | Pro | Ser | Arg | Leu | Pro | Gly | Pro | Pro | Asp | Thr | Pro |
|-----|-----|-----|-----|-----|-----|-----|-----|-----|-----|-----|-----|-----|-----|-----|-----|-----|
|     | 125 |     |     |     |     | 130 |     |     |     | 135 |     |     |     |     |     | 140 |

| Ile | Leu | Pro | Gln | Ser | Leu | Pro |
|-----|-----|-----|-----|-----|-----|-----|
|     |     |     | 145 |     |     |     | or

| Asp | Pro | Arg | Phe | Gln | Asp | Ser | Ser | Ser | Lys | Ala | Pro | Pro | Pro | Ser | Leu | Pro |
|-----|-----|-----|-----|-----|-----|-----|-----|-----|-----|-----|-----|-----|-----|-----|-----|-----|
| 112 |     |     | 115 |     |     |     |     | 120 |     |     |     |     | 125 |     |     |     |

| Ser | Pro | Ser | Arg | Leu | Pro | Gly | Pro | Pro | Asp | Thr | Pro | Ile | Leu | Pro | Gln | Ser |
|-----|-----|-----|-----|-----|-----|-----|-----|-----|-----|-----|-----|-----|-----|-----|-----|-----|
|     | 130 |     |     |     | 135 |     |     |     |     | 140 |     |     |     |     |     | 145 |

| Leu | Pro | Lys | Lys | Lys | Lys | Lys. |
|-----|-----|-----|-----|-----|-----|------|
|     |     |     |     | 150 |     |      |

17. The method according to claim 13, wherein said anti-hCG antibody is elicited with an immunogen selected form the group consisting of hCG and an hCG analyte-analog coupled to a carrier protein.

18. The method according to claim 17, wherein said hCG analyte-analog is the C-terminus peptide sequence 112–145 of β-hCG.

* * * * *

UNITED STATES PATENT AND TRADEMARK OFFICE
CERTIFICATE OF CORRECTION

PATENT NO. : 5,451,527
DATED : September 19, 1995
INVENTOR(S) : Virender K. Sarin, et al.

It is certified that error appears in the above-indentified patent and that said Letters Patent is hereby corrected as shown below:

Column 2, line 22, change "Phe$^{15}$" to --Phe$^{115}$--.

Column 2, line 24, change "Gln$^{145}$" to --Gln$^{145}$--.

Column 2, line 28, change "iwasa" to --Iwasa--.

Column 3, line 16, change "Asp-and" to --Asp and--.

Column 8, line 52, change "Ore." to --Org.--.

Column 10, line 37, change "Amine" to --Amino--.

UNITED STATES PATENT AND TRADEMARK OFFICE
CERTIFICATE OF CORRECTION

PATENT NO. : 5,451,527
DATED : September 19, 1995
INVENTOR(S) : Virender K. Sarin, *et al.*

It is certified that error appears in the above-indentified patent and that said Letters Patent is hereby corrected as shown below:

Column 11, line 68, change "Me." to

--Mo.--.

Column 12, line 9, change "(Spectra/per®," to

--Spectra/por®--.

Column 12, line 30, change "(rag)" to

--(mg)--.

Column 15, line 31, change "Sea" to

--Ser--.

Signed and Sealed this

Twenty-fourth Day of December, 1996

Attest:

BRUCE LEHMAN

*Attesting Officer*   *Commissioner of Patents and Trademarks*